United States Patent [19]

Vlasbloem et al.

[11] Patent Number: 4,984,258
[45] Date of Patent: Jan. 8, 1991

[54] APPARATUS FOR SLIT RADIOGRAPHY COMPRISING DISCRETE, CONTROLLABLE ATTENUATION ELEMENTS COACTING WITH A SLIT DIAPHRAGM

[75] Inventors: Hugo Vlasbloem, Maasland; Simon Duinker, Bloemendaal, both of Netherlands

[73] Assignee: B.V. Optische Industries "De Oude Delft", Delft, Netherlands

[21] Appl. No.: 125,214

[22] Filed: Nov. 25, 1987

Related U.S. Application Data

[63] Continuation of Ser. No. 713,309, Mar. 18, 1985.

[30] Foreign Application Priority Data

Mar. 16, 1984 [NL] Netherlands ............................ 8400845

[51] Int. Cl.⁵ ............................................... G21K 1/00
[52] U.S. Cl. ...................................... 378/145; 378/146; 378/152; 378/158
[58] Field of Search ........................... 378/145–148, 378/150–153, 156–158, ; 248/562, 626; 188/267, 269

[56] References Cited

U.S. PATENT DOCUMENTS

| | | | |
|---|---|---|---|
| 3,755,672 | 8/1973 | Edholm et al. | 378/151 |
| 3,806,062 | 4/1974 | Hofmann et al. | 188/267 |
| 3,868,082 | 2/1975 | Soderquist | 248/562 |
| 4,086,494 | 4/1978 | Malak | 378/153 |
| 4,099,063 | 7/1978 | Pury et al. | 378/176 |
| 4,128,767 | 12/1978 | Stödberg et al. | 378/153 |
| 4,490,835 | 12/1984 | Wons | 378/146 |

FOREIGN PATENT DOCUMENTS

| | | | |
|---|---|---|---|
| 2345406 | 7/1975 | Fed. Rep. of Germany | 378/150 |
| 1052756 | 11/1983 | U.S.S.R. | 248/562 |

*Primary Examiner*—Janice A. Howell
*Assistant Examiner*—David P. Porta
*Attorney, Agent, or Firm*—Louis E. Marn

[57] ABSTRACT

An apparatus for slit radiography comprising discrete controllable attenuation elements coacting with a slit diaphragm, each attenuation element being affixed to damping means.

9 Claims, 1 Drawing Sheet

APPARATUS FOR SLIT RADIOGRAPHY COMPRISING DISCRETE, CONTROLLABLE ATTENUATION ELEMENTS COACTING WITH A SLIT DIAPHRAGM

This is a continuation, of application Ser. No. 06/713,309, filed Mar. 18, 1985.

The present invention relates to an apparatus for slit radiography.

Such an apparatus, comprising discrete, controllable attenuation elements coacting with a slit diaphragm, is described in the copending Dutch patent application 8400845, which is incorporated herein by reference. Dutch patent application 8400845 describes various embodiments of suitable attenuation elements. Most of the attenuation methods described in Dutch patent application 8400845 are based on the use of juxtaposed, discrete elements made of X-ray attenuating material or coated with such a material, and which can each be moved, under the control of suitable control signals, at least partly into the X-ray beam passed through or to to be passed through the slit diaphragm and to a greater or lesser extent so as to attenuate said X-ray beam locally.

If use is made of such discrete elements, there is the risk that under the influence of the control signals, the elements get into a state of vibration in an undesirable manner or that the elements will overshoot their position when this is changed. Consequently, there is a need for means for damping oscillation or slipping of discrete attenuation elements.

It is an object of the present invention to satisfy this need. To this effect, according to the present invention, an apparatus of the above described type is characterized in that each controllable attenuation element is affixed to a damping member.

Some embodiments of the apparatus according to the present invention will now be described, by way of example, with reference to the accompanying drawing, in which:

FIG. 1 diagrammatically shows a first embodiment of an apparatus according to the present invention;

Figure 4:
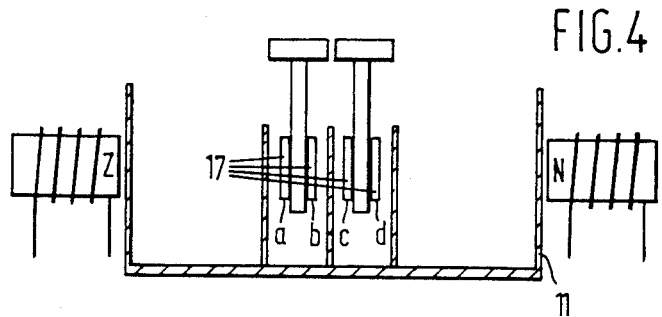

FIG. 4 diagrammatically shows a third embodiment of an apparatus according to the present invention.

FIG. 1A is a diagrammatic cross-sectional view of a slit diaphragm 1 having a slit S through which passes a substantially planar, fan-shaped X-ray beam B originating from an X-ray source 2 in operation in the manner as conventional in slit radiography.

Extending into the X-ray beam B, in operation, to a greater or lesser extent, is the free end of an elongate attenuation element 3 associated with a plurality of juxtaposed similar attenuation elements. Each attenuation element is adapted, in operation, to swivel relatively to a fixed point 5 according to an arrow 4 under the influence of control means not shown. Suitable control means are described in the copending Dutch patent application 8400845. Said control means do not form part of the present invention and will therefore not be further described herein.

Figure 1:
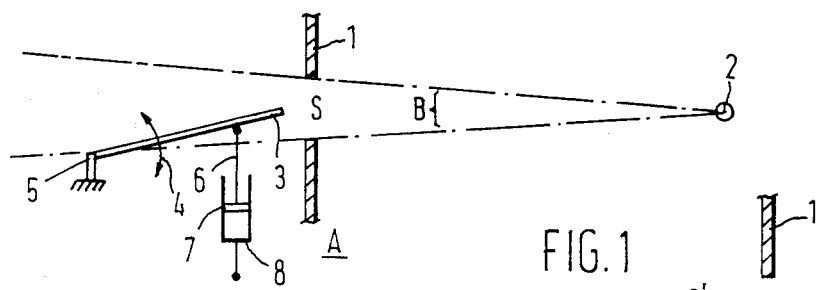

In the embodiment shown in FIG. 1, each attenuation element comprises a connecting rod 6 extending approximately transversely to the longitudinal direction of the attenuation element, the end of said rod distal from the attenuation element being connected to a piston 7 placed within a cylinder 8. Said cylinder is filled with a fluid in known manner, e.g. oil, braking the movement of the piston in the cylinder to some extent, so that oscillation or slipping of the attenuation element is prevented.

FIG. 1B shows a similar damping member used with a slide-like attenuation element 3'. The embodiments of the present invention to be described hereinafter can be employed accordingly both for slide-like and for elongate swivelling attenuation elements.

Figure 2:
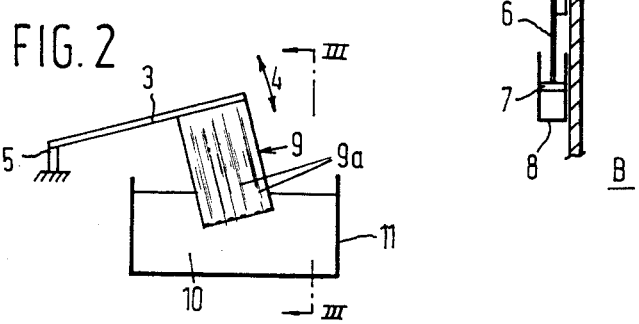
FIG. 2 is a diagrammatic side view of an apparatus according to the present invention.
Figure 3:
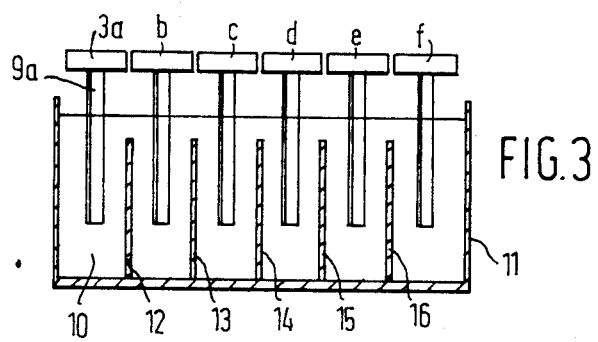
FIG. 3 is a cross-section on the line III—III of FIG. 2.

In the embodiment of the present invention shown in FIGS. 2 and 3, each attenuation element comprises a vane 9 extending into a vessel 11 fitted with a suitable liquid 10. As damping liquid may be used e.g. oil, alcohol or water.

The vane is made of rigid material and may be corrugated, as indicated by lines 9a. The vane may be connected to the attenuation element by gluing and is preferably made of synthetic plastics material. The vane may also be connected to the attenuation element by means of a connecting rod. Such an embodiment is particularly suitable for slide-like attenuation elements. Vessel 11 may be made of any suitable material. FIG. 3 shows the arrangement of FIG. 2 in front view, with the front wall of the vessel 11 being omitted. The attenuation elements 3a-3f are each provided with a vane 9a-9f extending into the liquid 10 in the vessel 11.

In order to prevent the vanes from influencing each other during movements of the associated attenuation elements, preferably parallel partitions 12-16 are disposed in the vessel, so that each vane extends into its own compartment of the vessel.

Partitions 12-16, moreover, increase the damping effect.

The extent of damping may be influenced by the choice of the viscosity of the liquid in the vessel, the height of the liquid level in the vessel and the form of the vane. If desired, the vessel can be filled with a plurality of layers of various poorly miscible liquids.

FIG. 4 shows a variant of FIGS. 2 and 3, wherein each vane is made of synthetic plastics material and is provided on both sides partly with a layer of electrically conductive material 17a-17d. For the sake of clearness, only two attenuation elements with vanes are shown. Adjacent the layers of conductive material, there is generated an inhomogeneous magnetic field oriented transversely to said vanes by means of magnet poles N and S provided on both sides of the vessel 11. The damping is obtained by eddy current losses occurring in the layers 17a-17d, as soon as said layers 17a-17d move relatively to the magnetic field (Foucault effect).

The vessel 11 in this case is preferably made of copper.

The damping method by means of eddy current losses can be employed separately or, as shown in FIG. 4, in combination with a vessel containing liquid, also having a damping effect.

It is observed that various modifications will readily occur to one skilled in the art after the foregoing. For instance, it is possible to provide the attenuation elements with electrically conductive metal vanes wherein eddy current losses occur under the influence of an inhomogeneous magnetic field. In that case, the layers 17 can be omitted from the embodiment shown in FIG. 4.

Use could also be made of a vane of electrically non-conductive material provided with a conductive layer on one side only. Such modifications are deemed not to depart from the scope of the present invention.

What we claim:

1. An apparatus for slit radiography, which comprises:

an X-ray source:

an X-ray detector for collecting radiation passing through a body to be radiographed;

a slit diaphragm positioned between said X-ray source and said body for forming a substantially planar X-ray beam;

means for scanning said body with said planar X-ray beam;

a plurality of attenuating elements positioned along said slit diaphragm, each of said attenuating elements having a free end extendable into and thereby attenuating said planar X-ray beam;

control means for extending said free ends of said attenuating elements into and out of said planar X-ray beam during scanning of said body with said planar X-ray beam; and a dampening assembly affixed to each of said attenuating elements to prevent oscillation of each of said attenuating elements as a result of extension into and out of said planar X-ray beam during scanning of said body with said X-ray beam.

2. The apparatus as defined in claim 1 wherein said dampening assembly includes a piston disposed in a fluid-filled cylinder.

3. The apparatus as defined in claim 1 wherein said dampening assembly is a vane extending into a vessel containing liquid.

4. An apparatus according to claim 3, characterized in that the vane is corrugated.

5. An apparatus according to claim 3, characterized in that the vessel comprises partitions forming juxtaposed compartments, a vane of an attenuation element extending into each compartment.

6. An apparatus according to claim 5, characterized in that each vane is provided on at least one side at least partly with electrically conductive material and that means are provided for generating an inhomogeneous magnetic field oriented transversely to the vanes.

7. An apparatus according to claim 6, characterized in that the vanes are made of electrically conductive material and that means are provided for generating an inhomogeneous magnetic field oriented transversely to the vanes.

8. The apparatus as defined in claim 1 wherein each attenuation element comprises a vane of electrically non-conductive material provided on at least one side thereof with a layer of electrically conductive material and that means are provided for generating an inhomogeneous magnetic field oriented transversely to said vanes.

9. The apparatus as defined in claim 1 wherein each attenuation element comprises a vane of electrically conductive material and means are provided for generating an inhomogeneous magnetic field oriented transversely to said vanes.

* * * * *